United States Patent
Castro Pineiro

(10) Patent No.: US 7,300,955 B2
(45) Date of Patent: Nov. 27, 2007

(54) METHOD AND MATERIALS FOR TREATMENT OF ALZHEIMER'S DISEASE

(75) Inventor: Jose Luis Castro Pineiro, Bishops Stortford (GB)

(73) Assignee: Merck Sharp + Dohme Ltd., Hoddesdon, Hertfordshire (GB)

( * ) Notice: Subject to any disclaimer, the term of this patent is extended or adjusted under 35 U.S.C. 154(b) by 693 days.

(21) Appl. No.: 10/789,008

(22) Filed: Feb. 27, 2004

(65) Prior Publication Data

US 2004/0171683 A1 Sep. 2, 2004

(30) Foreign Application Priority Data

Feb. 27, 2003 (GB) ................... 0304524.2

(51) Int. Cl.
*A61K 31/19* (2006.01)
*A61K 31/216* (2006.01)
*C07C 313/02* (2006.01)
*C07C 317/12* (2006.01)
*C07C 317/14* (2006.01)

(52) U.S. Cl. ......................... 514/506; 514/570; 558/61

(58) Field of Classification Search ................ 558/488; 546/290; 548/243, 316.4, 263.2, 541; 544/239; 549/62, 475

See application file for complete search history.

(56) References Cited

U.S. PATENT DOCUMENTS

2003/0114496 A1 * 6/2003 Churcher et al.

* cited by examiner

*Primary Examiner*—Kamal A. Saeed
*Assistant Examiner*—Janet L Coppins
(74) *Attorney, Agent, or Firm*—William Krovatin; John C. Todaro

(57) ABSTRACT

The invention provides the combined use of an inhibitor of formation or release of β-amyloid and a nitric oxide releaser for the treatment or prevention of Alzheimer's disease.

8 Claims, No Drawings

METHOD AND MATERIALS FOR TREATMENT OF ALZHEIMER'S DISEASE

CROSS REFERENCE TO RELATED APPLICATIONS

This application claims priority under 35 U.S.C. § 119 from GB Application No. 0304524.2, filed Feb. 27, 2003.

The present invention relates to a novel method of treating Alzheimer's disease, and to novel compounds, their salts and pharmaceutical compositions comprising them suitable for use in the said method. In particular, the invention relates to methods for the treatment or prevention of Alzheimer's disease which combine nitric oxide release with the inhibition of the formation or release of β-amyloid.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ). The role of secretases, including the putative γ-secretase, in the processing of amyloid precursor protein (APP) to form Aβ is well documented in the literature and is reviewed, for example, in WO 01/70677.

One approach to the treatment or prevention of Alzheimer's disease involves inhibition of the formation or release of Aβ, e.g by inhibition of one or more of the secretases, in particular γ-secretase. Compounds which inhibit γ-secretase are disclosed in WO 03/018543, U.S. 2003/0114496, WO 01/53255, WO 01/66564, WO 01/70677, WO 01/90084, WO 01/77144, WO 02/30912, WO 02/36555, WO 02/081435 and WO 02/081433. Other compounds which inhibit the formation or release of Aβ include those disclosed in WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, U.S. 2002/0025955 and U.S. 2002/0022621.

An alternative approach to the treatment of Alzheimer's disease involves administering anti-inflammatory agents (especially NSAIDs) with a view to counteracting the neurotoxic effects of secreted Aβ. According to several reports (e.g. Jantzen et al, *J. Neuroscience*, 2002, 26, 2246-54; Wenk et al, *Eur. J. Pharmacol.*, 2002, 453, 319-24; and WO 02/092072), improved results are obtained using NSAIDs which are capable of releasing nitric oxide (NO) subsequent to administration.

According to the present invention there is provided a method for the treatment or prevention of Alzheimer's disease comprising administering to a subject in need thereof a therapeutically-effective amount of a compound which inhibits the formation or release of β-amyloid and a therapeutically-effective amount of a nitric oxide releaser.

Any compound known to release NO subsequent to administration to a human or animal subject may be used in the invention. Such compounds are well known in the art, and are typically nitrate esters of alkanols. Likewise, any of the known inhibitors of the formation or release of Aβ may be used, such as the compounds disclosed in WO 03/018543, U.S. 2003/0114496, WO 01/53255, WO 01/66564, WO 01/70677, WO 01/90084, WO 01/77144, WO 02/30912, WO 02/36555, WO 02/081435, WO 02/081433, WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, U.S. 2002/0025955 and U.S. 2002/0022621. Preferred inhibitors of the formation or release of Aβ, for use in the method according to the invention, include the compounds disclosed in WO 03/018543 and U.S. 2003/0114496, the contents of which are incorprated herein by reference.

Preferably said inhibitor and said nitric oxide releaser are administered simultaneously, and advantageously said inhibitor and said nitric oxide releaser are combined in a single dosage formulation, or are combined in one and the same chemical compound. Such a chemical compound is typically a compound of formula I:

$$R-CH_2-ONO_2 \qquad \qquad I$$

where R is such that R—CH$_2$OH or R—CHO is an inhibitor of the formation or release of Aβ;

or a pharmaceutically acceptable salt thereof.

R may be such that R—CH$_2$OH or R—CHO belongs to any of the classes of inhibitor disclosed in the above-listed patent applications, but preferably R—CH$_2$OH or R—CHO is a γ-secretase inhibitor, e.g. of the type disclosed in WO 02/36555 or WO 02/081435 and most preferably of the type disclosed in WO 03/018453 or U.S. 2003/0114496.

The invention also extends to novel compounds, suitable for use in the above method, which combine NO-releasing activity with a capability for γ-secretase inhibition. In particular, there is provided a compound of formula II:

$$Ar^1SO_2 \underset{Ar^2}{\overset{R^{1c}}{\diagdown}} \cdots \overset{O}{\underset{R^{1b}}{\diagdown}} (L)_n-(CH_2)_p-ONO_2 \qquad II$$

wherein:
m is 0 or 1;
n is 0 or 1;
p is an integer in the range 1-6;
L is a linking group;
$R^{1b}$ represents H, $C_{1-4}$alkyl or OH;
$R^{1c}$ represents H or $C_{1-4}$alkyl;
$Ar^1$ and $Ar^2$ independently represent phenyl or heteroaryl, either of which bears 0-3 substituents independently selected from halogen, CN, NO$_2$, CF$_3$, CHF$_2$, OH, OCF$_3$, CHO, CH═NOH, $C_{1-4}$alkoxy, $C_{1-4}$alkoxycarbonyl, $C_{2-6}$acyl, $C_{2-6}$alkenyl and $C_{1-4}$alkyl which optionally bears a substituent selected from halogen, CN, NO$_2$, CF$_3$, OH and $C_{1-4}$alkoxy;

or a pharmaceutically acceptable salt thereof.

As used herein, the expression "hydrocarbon group" refers to groups consisting solely of carbon and hydrogen atoms. Such groups may comprise linear, branched or cyclic structures, singly or in any combination consistent with the indicated maximum number of carbon atoms, and may be saturated or unsaturated, including aromatic when the indicated maximum number of carbon atoms so permits.

As used herein, the expression "$C_{1-x}$alkyl" where x is an integer greater than 1 refers to straight-chained and branched alkyl groups wherein the number of constituent carbon atoms is in the range 1 to x. Particular alkyl groups include methyl, ethyl, n-propyl, isopropyl and t-butyl. Derived expressions such as "$C_{2-6}$alkenyl", "hydroxy$C_{1-6}$alkyl", "heteroaryl" $C_{1-6}$alkyl, "$C_{2-6}$alkynyl" and "$C_{1-4}$alkoxy" are to be construed in an analogous manner.

The expression "$C_{6-10}$aryl" as used herein includes phenyl and naphthyl. Phenyl is preferred.

The expression "heteroaryl" as used herein means a cyclic or polycyclic system of up to 10 ring atoms selected from C, N, O and S, wherein at least one of the constituent rings is aromatic and comprises at least one ring atom which is other than carbon. Where a heteroaryl ring comprises two or more atoms which are not carbon, not more than one of said atoms may be other than nitrogen. Preferred heteroaryl groups contain 5 or 6 ring atoms in total. Examples of heteroaryl groups include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. Further examples of heteroaryl groups include tetrazole, 1,2,4-triazine and 1,3,5-triazine.

The term "halogen" as used herein includes fluorine, chlorine, bromine and iodine, of which fluorine and chlorine are preferred.

For use in medicine, the compounds of formula II may advantageously be in the form of pharmaceutically acceptable salts. Other salts may, however, be useful in the preparation of the compounds of formula II or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, benzenesulphonic acid, methanesulphonic acid, fumaric acid, maleic acid, succinic acid, acetic acid, benzoic acid, oxalic acid, citric acid, tartaric acid, carbonic acid or phosphoric acid. Alternatively, where the compounds of the invention carry an acidic moiety, pharmaceutically acceptable salts may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula II, m and n are independently 0 or 1, but m is preferably 1. Suitable values for p are in the range 1-6, especially 3-5, and most preferably p is 4.

L (when present) represents a bivalent linking group, typically comprising up to 20 (preferably up to 15) skeletal atoms selected from carbon and oxygen. In one embodiment, L comprises an optionally-substituted hydrocarbon residue linked to the —$(CH_2)_n ONO_2$ moiety by an ester group, and may be represented by the formula:

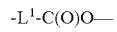

-$L^1$-C(O)O— wherein $L^1$ is a hydrocarbon residue of up to 10 carbon atoms, optionally bearing up to 3 substituents selected from halogen, CN, OH and $C_{1-4}$alkoxy. In a preferred embodiment, $L^1$ represents:

—Ar—CH=CH— wherein Ar is a phenyl group bearing up to 2 substituents selected from hydroxy and methoxy. In a particularly preferred embodiment, L represents:

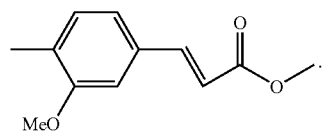

$R^{1c}$ represents H or $C_{1-4}$alkyl, such as methyl or ethyl, but preferably represents H.

$R^{1b}$ represents H, $C_{1-4}$alkyl or OH, but preferably represents H.

In a particular embodiment, m is 1 and $R^{1b}$ and $R^{1c}$ are both H.

$Ar^1$ and $Ar^2$ independently represent optionally-substituted phenyl or heteroaryl. Typical heteroaryl embodiments of $Ar^1$ include optionally substituted pyridyl, in particular optionally substituted 3-pyridyl. $Ar^1$ is preferably selected from 5-(trifluoromethyl)-3-pyridyl and phenyl which is optionally substituted in the 4-position with halogen, CN, vinyl, allyl, acetyl, methyl or mono-, di- or trifluoromethyl. In one preferred embodiment of the invention $Ar^1$ is selected from 4-chlorophenyl, 4-trifluoromethylphenyl and 5-(trifluoromethyl)-3-pyridyl.

$Ar^2$ preferably represents phenyl bearing at least one substituent as defined previously, in particular phenyl bearing 2 or 3 substituents selected from halogen, CN, $CF_3$ and optionally-substituted alkyl. $Ar^2$ is typically selected from phenyl groups bearing halogen substituents (preferably fluorine) in the 2- and 5-positions, in the 2- and 6-positions or in the 2-, 3- and 6-positions, or from phenyl groups bearing a fluorine substituent in the 2-position and halogen, CN, methyl or hydroxymethyl in the 5-position. In a preferred embodiment of the invention, $Ar^2$ represents 2,5-difluorophenyl, 2,6-difluorophenyl or 2,3,6-trifluorophenyl.

In a particular embodiment, $Ar^1$ is 4-chlorophenyl or 4-trifluoromethylphenyl and $Ar^2$ is 2,5-difluorophenyl.

Examples of compounds in accordance with the invention include:

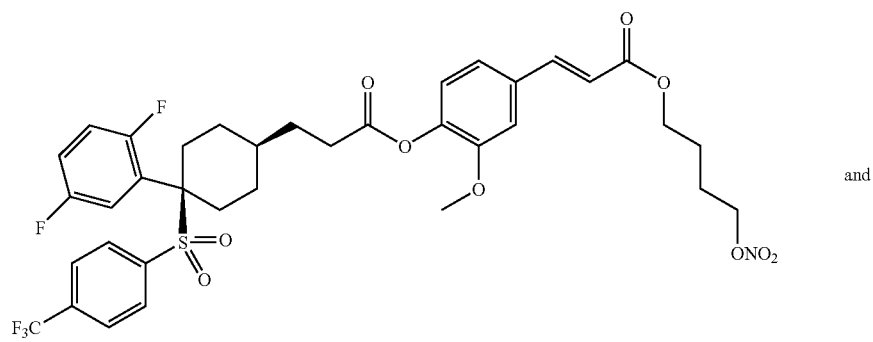

and

-continued

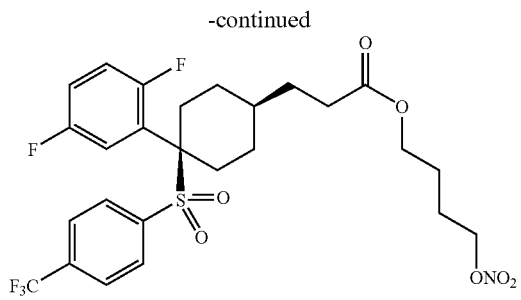

and pharmaceutically acceptable salts thereof.

The compounds of the present invention have an activity as inhibitors of γ secretase.

The invention also provides pharmaceutical compositions comprising one or more compounds of formula II (or pharmaceutically acceptable salts thereof) and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 250 mg, for example 5, 10, 25, 50, 100 or 200 mg, of the active ingredient. Tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

The present invention also provides a compound of formula II or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of formula II or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound of formula II or a pharmaceutically acceptable salt thereof.

For treating or preventing Alzheimer's disease, the optimum dosage level of the compounds of formula II, in terms of safety and efficacy, may vary according to the severity of the disease and/or other factors specific to the individual patient, and may be determined by methods well known to those skilled in the art. Generally speaking, doses of about 0.1 to 250 mg/kg per day, preferably about 0.5 to 100 mg/kg per day, more preferably about 1 to 50 mg/kg of body weight per day, may be contemplated. The compounds may be administered on any suitable regimen, for example 1 to 4 times per day. However, other regimens and/or dosage levels outside the limits outlined above may be used if circumstances so demand.

For treatment or prevention of Alzheimer's disease by administration of prior art compounds which are modified so as to release NO or which are administered in combination with a separate NO-releaser, suitable dosage levels and frequencies will be in line with the values recommended for the unmodified compounds in question, used alone.

Compounds of formula II may be prepared by reaction of a compound of formula III with silver nitrate:

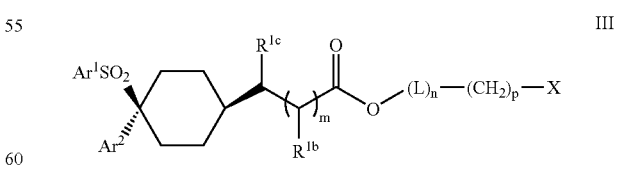

III where X represents chlorine, bromine or iodine, and m, n, p, L, $R^{1b}$, $R^{1c}$, $Ar^1$ and $Ar^2$ have the same meanings as before. The reaction takes place in refluxing acetonitrile with protection from light.

Compounds of formula III may be prepared by coupling of acids IV with HO-$(L)_n$-$(CH_2)_p$—X:

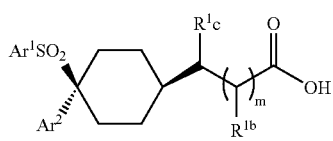

where X, m, n, p, L, $R^{1b}$, $R^{1c}$, $Ar^1$ and $Ar^2$ have the same meanings as before. Any of the known techniques of esterification may be used, such as conversion of acids IV to the corresponding acid chlorides prior to treatment with the relevant hydroxy compound in the presence of base.

Compounds of formula III in which n is 1 and L is -$L^1$-C(O)O— may alternatively be prepared by esterifying an acid IV with HO-$L^1$-$CO_2$H, then esterifying the product with HO—$(CH_2)_p$—X, where $L^1$ and X have the same meanings as before.

The acids IV may be prepared as described in WO 02/081435.

It will be appreciated by those skilled in the art that a given compound in accordance with formula II may be converted into another compound also in accordance with formula I by means of standard synthetic techniques such as alkylation, oxidation, reduction, esterification, amide coupling, hydrolysis, electrophilic substitution and nucleophilic substitution. Alternatively, such conversions may be carried out on synthetic precursors of the compounds of formula II.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary. Alternatively, such techniques may be carried out on racemic synthetic precursors of the compounds of interest.

Where they are not commercially available, the starting materials and reagents used in the above-described synthetic schemes may be prepared by conventional means.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, 3$^{rd}$ Ed., John Wiley & Sons, 1999. The protecting groups may be removed at a convenient subsequent stage using methods known from the art.

An assay which can be used to determine the level of activity of compounds of the present invention is described in WO01/70677. A preferred assay to determine such activity is as follows:

1) SH-SY5Y cells stably overexpressing the βAPP C-terminal fragment SPA4CT, are cultured at 50-70% confluency. 10 mM sodium butyrate is added 4 hours prior to plating.
2) Cells are plated in 96-well plates at 35,000 cells/well/100 μL in Dulbeccos minimal essential medium (DMEM) (phenol red-free)+10% foetal bovine serum (FBS), 50 mM HEPES buffer (pH7.3), 1% glutamine.
3) Make dilutions of the compound plate. Dilute stock solution 18.2× to 5.5% DMSO and 11× final compound concentration. Mix compounds vigorously and store at 4° C. until use.
4) Add 10 μL compound/well, gently mix and leave for 18 h at 37° C., 5% $CO_2$.
5) Prepare reagents necessary to determine amyloid peptide levels, for example by Homogeneous Time Resolved Fluorescence (HTRF) assay.
6) Plate 160 μL aliquots of HTRF reagent mixture to each well of a black 96-well HTRF plate.
7) Transfer 40 μL conditioned supernatant from cell plate to HTRF plate. Mix and store at 4° C. for 18 hours.
8) To determine if compounds are cytotoxic following compound administration, cell viability is assessed by the use of redox dye reduction. A typical example is a combination of redox dye MTS (Promega) and the electron coupling reagent PES. This mixture is made up according to the manufacturer's instructions and left at room temperature.
9) Add 10 μL/well MTS/PES solution to the cells; mix and leave at 37° C.
10) Read plate when the absorbance values are approximately 0.4-0.8. (Mix briefly before reading to disperse the reduced formazan product).
11) Quantitate amyloid beta 40 peptide using an HTRF plate reader.

Alternative assays are described in *Biochemistry*, 2000, 39(30), 8698-8704.

See also, *J. Neuroscience Methods*, 2000, 102, 61-68.

The compounds of the present invention generally show high potency as measured by the above assays. Thus the following Examples all had an $ED_{50}$ of less than 1 μM, typically less than 250 nM, and frequently less than 100 nM in at least one of the above assays.

The following examples illustrate the present invention.

EXAMPLE 1

Cis 4-(nitrooxy)butyl 3-(4-(2,5-difluorophenyl)-4-{[4(trifluoromethyl) phenyl]sulfonyl}cyclohexyl)propanoate Step 1: Cis-4-bromobutyl 3-(4-(2,5-difluorophenyl)-4-{[4-(trifluoromethyl) phenyl]sulfonyl}cyclohexyl)propanoate

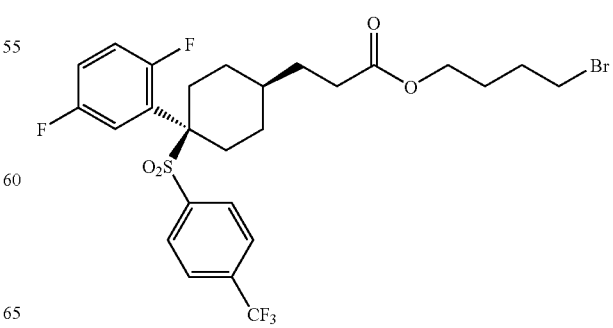

Sodium hydride (60% dispersion in oil, 32 mg, 0.8 mmol) was added to a stirred solution of cis-3-(4-(2,5-difluorophenyl)-4-{[4-(trifluoromethyl) phenyl]sulfonyl}cyclohexyl) propanoic acid (300 mg, 0.63 mmol) (prepared by the methods disclosed in WO 02/081435) in dry DMF (5 mL) at room temperature under nitrogen. After 90 minutes, 1,4-dibromobutane (150 μL, 1.3 mmol) was added. After stirring at room temperature overnight the reaction was quenched with water. The mixture was extracted with ethyl acetate (×3). The combined extracts were washed with brine (×1), then dried (Na₂SO₄), filtered and evaporated. The residue was purified by chromatography on silica, eluting with 10 to

EXAMPLE 2

Cis-4-(nitrooxy)butyl (2E)-3-(4-{[3-(4-(2,5-difluorophenyl)-4-{[4-(trifluoromethyl)phenyl]sulfonyl}cyclohexyl)propanoyl]oxy}-3-methoxyphenyl)prop-2-enoate Step 1: Cis-4-bromobutyl (2E)-3-(4-{[3-(4-(2,5-difluorophenyl)-4-{[4-(trifluoromethyl)phenyl]sulfonyl}cyclohexyl)propanoyl]oxy}-3-methoxyphenyl)prop-2-enoate

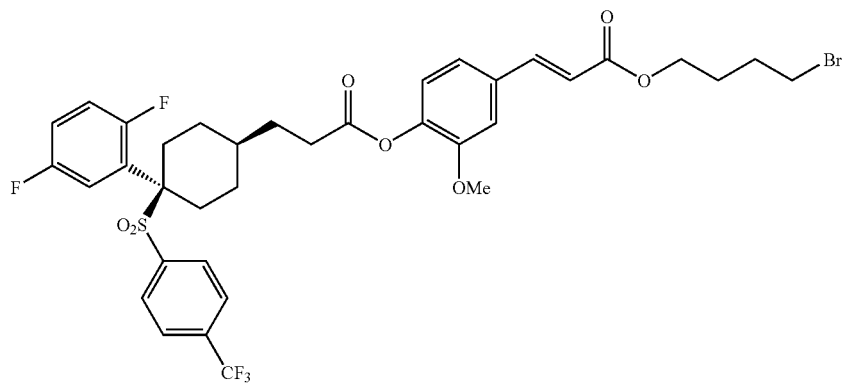

20% ethyl acetate/hexanes to give the bromo-ester (312 mg, 81%). MS (ES+) 635 ([M+Na]⁺), 633 ([M+Na]⁺), 613 ([MH]⁺), 611 ([MH]⁺).

Step 2: Cis 4-(nitrooxy)butyl 3-(4-(2,5-difluorophenyl)-4-{[4(trifluoromethyl) phenyl]sulfonyl}cyclohexyl)propanoate

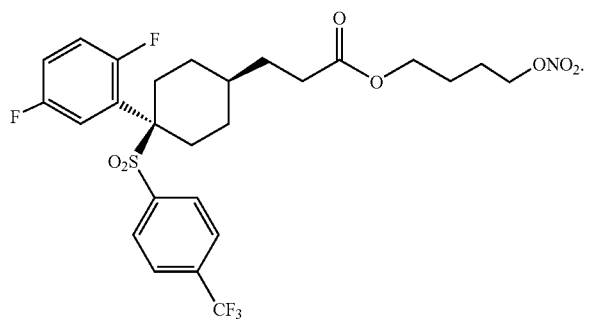

A mixture of the bromide from Step 1 (300 mg, 0.49 mmol) and silver nitrate (170 mg, 1.0 mmol) in dry acetonitrile (5 mL) was stirred and heated at reflux, protected from light, for two hours. After cooling to room temperature, the reaction mixture was diluted with ethyl acetate and filtered. The filtrate was evaporated and purified by chromatography on silica, eluting with 10 to 20 to 40% ethyl acetate/hexanes to give the title compound (217 mg, 75%) as an oil. δ (¹H, 360 MHz, CDCl₃) 1.43-1.62 (3H, m), 1.68-1.89 (8H, m), 2.30-2.52 (6H, m), 4.12 (2H, t, J=6.1), 4.50 (2H, t, J=6.1), 6.76-6.84 (1H, m), 7.00-7.10 (2H, m), 7.53 (2H, d, J=8.2), 7.65 (2H, d, J=8.2); MS (ES+) 616 ([M+Na]⁺).

N,N-Dimethylformamide (1 drop) was added to a stirred solution of cis-3-(4-(2,5-difluorophenyl)-4-{[4-(trifluoromethyl)phenyl]sulfonyl}cyclohexyl) propanoic acid (300 mg, 0.63 mmol) and oxalyl chloride (120 μL, 1.4 mmol) in dry dichloromethane (5 mL) at room temperature. After two hours at room temperature, the volatiles were removed in vacuo. The residue was taken up in dry dichloromethane (2 mL) under nitrogen. 4-Hydroxy-3-methoxycinnamic acid (120 mg, 0.63 mmol) and then pyridine (250 μL, 3.1 mmol) were added. The mixture was stirred at room temperature overnight, then quenched with methanol (5 mL). The volatiles were removed in vacuo. The residue was partitioned between ethyl acetate and hydrochloric acid (1N). The aqueous layer was extracted with ethyl acetate (×2). The combined organic extracts were washed with brine (×1), then dried (Na₂SO₄), filtered and evaporated. Partial purification by chromatography on silica, eluting with 50% ethyl acetate/hexanes+1% acetic acid gave the crude cinnamic acid (387 mg). This material was used without further purification.

Sodium hydride (60% dispersion, 32 mg, 0.8 mmol) was added to a stirred solution of the crude acid from above (329 mg) in dry DMF (2 mL) at room temperature under nitrogen. After two hours 1,4-dibromobutane (150 μL, 1.3 mmol) was added. The mixture was stirred at room temperature overnight, then quenched with water and extracted with ethyl acetate (×3). The combined extracts were washed with brine (×1), dried (Na₂SO₄), filtered and evaporated. The residue was purified by chromatography on silica, eluting with 10% to 20% to 30% ethyl acetate/hexanes to give the bromide (123 mg, 25% over 2 steps) as an oil. δ (1H, 400 MHz, CDCl₃) 1.49-1.59 (2H, m), 1.68-2.05 (9H, m), 2.40-2.55 (4H, m), 2.62 (2H, t, J=7.6), 3.47 (2H, t, J=6.6), 3.86 (3H, s), 4.25 (2H, t, J=6.3), 6.38 (1H, d, J=16.0), 6.78-6.84 (1H, m), 7.02-7.15 (5H, m), 7.54 (2H, d, J=8.2), 7.62-7.67 (3H, m); MS (ES+) 789 ([MH]+), 787 ([MH]+).

Step 2: 4-(nitrooxy)butyl (2E)-3-(4-{[3-(4-(2,5-difluorophenyl)-4-{[4-(trifluoromethyl)phenyl]sulfonyl}cyclohexyl)propanoyl]oxy}-3-methoxyphenyl)prop-2-enoate

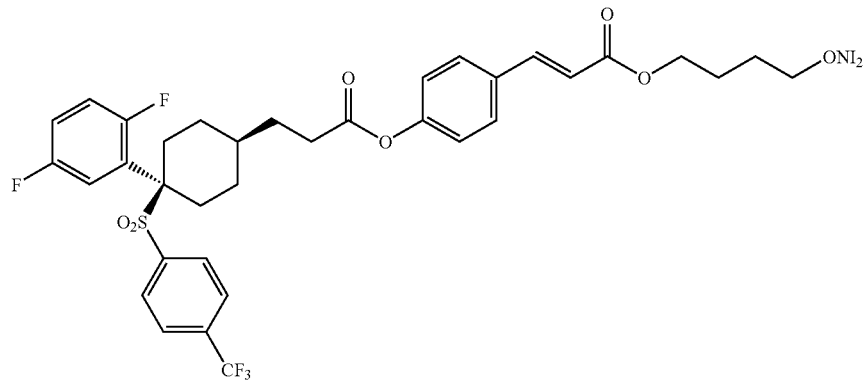

A mixture of the bromide from step 1 (105 mg, 0.13 mmol) and silver nitrate (45 mg, 0.26 mmol) in dry acetonitrile (1 mL) was stirred and heated at reflux under nitrogen, protected from light, for two hours. After cooling to room temperature the mixture was diluted with ethyl acetate and filtered. The filtrate was evaporated. The residue was purified by chromatography, eluting with 10% to 20% to 30% ethyl acetate/hexanes to give desired product (92 mg, 92%) as a foam. δ ($^1$H, 400 MHz, CDCl$_3$) 1.50-1.60 (2H, m), 1.68-1.99 (9H, m), 2.40-2.55 (4H, m), 2.62 (2H, t, J =7.6), 3.86 (3H, s), 4.26 (2H, t, J=5.9), 4.53 (2H, t, J=6.1), 6.38 (1H, d, J=16.0), 6.79-6.84 (1H, m), 7.03-7.14 (5H, m), 7.54 (2H, d, J=8.2), 7.63-7.67 (3H, m); MS (ES+) 770 ([MH]+).

What is claimed is:

1. A compound of formula II:

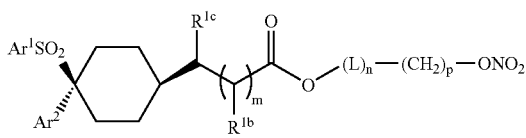

II wherein:

m is 0 or 1;
n is 0 or 1;
p is an integer in the range 1-6;
L is a bivalent linking group comprising up to 20 skeletal atoms selected from carbon and oxygen;
$R^{1b}$ represents H, $C_{1-4}$alkyl or OH;
$R^{1c}$ represents H or $C_{1-4}$alkyl;
$Ar^1$ and $Ar^2$ independently represent phenyl or heteroaryl, either of which bears 0-3 substituents independently selected from halogen, CN, $NO_2$, $CF_3$, $CHF_2$, OH, $OCF_3$, CHO, CH=NOH, $C_{1-4}$alkoxy, $C_{1-4}$alkoxycarbonyl, $C_{2-6}$acyl, $C_{2-6}$alkenyl and $C_{1-4}$alkyl which optionally bears a substituent selected from halogen, CN, $NO_2$, $CF_3$, OH and $C_{1-4}$alkoxy;

or a pharmaceutically acceptable salt thereof.

2. A compound according to claim 1 wherein m is 1 and $R^{1b}$ and $R^{1c}$ are both H.

3. A compound according to claim 1 wherein $Ar^1$ is 4-chlorophenyl or 4-trifluoromethylphenyl and $Ar^2$ is 2,1-difluorophenyl.

4. A compound according to claim 1 wherein L is represented by the formula:

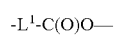

wherein $L^1$ is a hydrocarbon residue of up to 10 carbon atoms, optionally bearing up to 3 substituents selected from halogen, CN, OH and $C_{1-4}$alkoxy.

5. A compound according to claim 4 wherein $L^1$ represents

wherein Ar is a phenyl group bearing up to 2 substituents selected from hydroxy and methoxy.

6. A compound according to claim 1 wherein L represents:

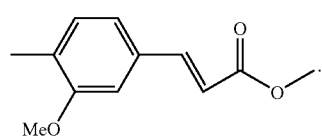

7. A compound according to claim 1 selected from:
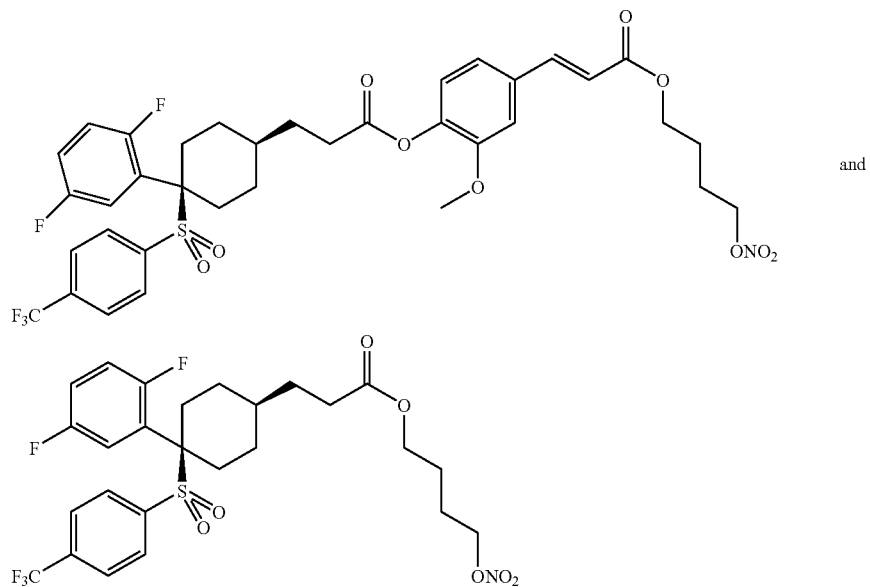
and pharmaceutically acceptable salts thereof.
8. A pharmaceutical composition comprising a compound according to claim 1 and a pharmaceutically acceptable carrier.
* * * * *